(12) United States Patent
Johnson et al.

(10) Patent No.: US 11,030,509 B1
(45) Date of Patent: Jun. 8, 2021

(54) BIODEGRADABLE PAYMENT CARD WITH EMBEDDED PLANT SEEDS

(71) Applicant: Capital One Services, LLC, McLean, VA (US)

(72) Inventors: Benal Johnson, Arlington, VA (US); William Carroll, Huntingtown, MD (US)

(73) Assignee: Capital One Services, LLC, McLean, VA (US)

( * ) Notice: Subject to any disclaimer, the term of this patent is extended or adjusted under 35 U.S.C. 154(b) by 0 days.

(21) Appl. No.: 16/910,506

(22) Filed: Jun. 24, 2020

(51) Int. Cl.
*G06K 19/077* (2006.01)
*G06K 19/06* (2006.01)

(52) U.S. Cl.
CPC . *G06K 19/07722* (2013.01); *G06K 19/06196* (2013.01)

(58) Field of Classification Search
CPC ........ G06K 19/06196; G06K 19/07722; B32B 2425/00
USPC .................................. 235/492, 493
See application file for complete search history.

(56) References Cited

U.S. PATENT DOCUMENTS

| | | | | |
|---|---|---|---|---|
| 5,255,941 A * | 10/1993 | Solomon | ................. | B42D 25/20 283/82 |
| 5,786,408 A | 7/1998 | Kuroda et al. | | |
| 6,193,163 B1 * | 2/2001 | Fehrman | ............... | G06K 19/077 235/441 |
| 7,735,250 B2 | 6/2010 | Menzie et al. | | |
| 10,614,449 B1 * | 4/2020 | Pham | ................ | G06K 19/07703 |
| 10,817,868 B1 * | 10/2020 | Marsch | ................ | G06Q 20/347 |
| 2003/0178495 A1 * | 9/2003 | Jones | ............... | G06K 19/07745 235/492 |
| 2009/0008462 A1 * | 1/2009 | Jensen | ................. | B42D 15/045 235/494 |
| 2010/0078489 A1 * | 4/2010 | Winkler | ............... | B42D 25/369 235/493 |
| 2017/0109743 A1 * | 4/2017 | Zarakas | ............. | G06Q 20/3552 |

FOREIGN PATENT DOCUMENTS

JP          2005007695 A  *  1/2005

OTHER PUBLICATIONS

Machine translation of JP2005007695 from European Patent Office, retrieved Dec. 29, 2020 (Year: 2020).*

* cited by examiner

*Primary Examiner* — Suezu Ellis

(74) *Attorney, Agent, or Firm* — Banner & Witcoff, Ltd.

(57) ABSTRACT

Aspects described herein may allow for a payment card assembly including a payment card having a first surface and an opposed second surface, and being formed of a biodegradable plastic. A Europay, Mastercard, and Visa (EMV) chip may be removably secured to the payment card. One or more plant seeds may be embedded in the payment card.

18 Claims, 2 Drawing Sheets

US 11,030,509 B1

BIODEGRADABLE PAYMENT CARD WITH EMBEDDED PLANT SEEDS

FIELD OF USE

Aspects of the disclosure relate generally to a payment card formed of a biodegradable plastic with one or more plant seeds embedded therein. More specifically, aspects of the disclosure may provide for a payment card formed of a biodegradable plastic, a Europay, Mastercard, and Visa (EMV) chip removably secured to the card, and one or more plant seeds embedded in the payment card.

BACKGROUND

When payment cards, such as credit cards, expire, or are no longer in use, they are typically thrown in the trash, and eventually end up in landfills.

SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below.

Aspects discussed herein may provide a payment card assembly including a payment card having a first surface and an opposed second surface, and being formed of a biodegradable plastic. An EMV chip is removably secured to the payment card. One or more plant seeds is embedded in the payment card.

In accordance with certain aspects, a payment card assembly includes a payment card having a first surface, and an opposed second surface, and formed of a plurality of layers of biodegradable plastic. An EMV chip is removably secured on the first surface of the payment card. A magnetic strip is removably secured on the second surface of the payment card. One or more plant seeds is embedded in the payment card.

In accordance with other aspects, a payment card assembly includes a payment card having a first surface, an opposed second surface, a first recess formed in the first surface, and a second recess formed in the second surface, and is formed of a plurality of layers of biodegradable plastic. An EMV chip is removably secured in the first recess. A magnetic strip is removably secured in the second recess. A plurality of plant seeds is embedded in a first layer of the plurality of layers of biodegradable plastic, the first layer being adjacent an outermost layer of the plurality of layers of biodegradable plastic.

By embedding plant seeds within a payment card formed of biodegradable plastic and removably securing an EMV chip and a magnetic strip to the payment card, the user can remove the EMV chip and magnetic strip when the card is no longer active. The card can then be placed in soil, where the payment card may decompose and the plant seeds may grow into a plant, thereby helping the environment by reducing the amount of discarded material and creating a growing plant. These features, along with many others, are discussed in greater detail below.

BRIEF DESCRIPTION OF THE DRAWINGS

The present disclosure is illustrated by way of example and not limited in the accompanying figures in which like reference numerals indicate similar elements and in which.

DETAILED DESCRIPTION

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof.

Embodiments discussed herein depict a payment card formed of a biodegradable plastic with one or more plant seeds embedded in the payment card. Exemplary payment cards can include credit cards, debit cards, ATM cards, and money access cards ("MAC"). A payment card may include an EMV chip and/or a magnetic strip.

Figure 1:
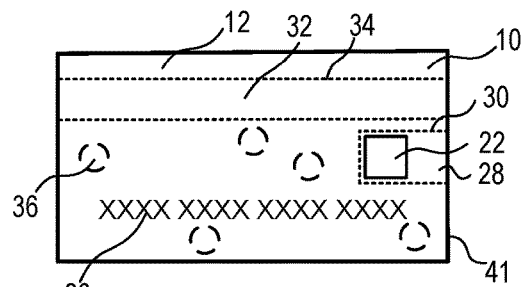
FIG. 1 depicts a front plan view of an example of a payment card with an EMV chip and one or more plant seeds embedded in the payment card.
Figure 2:
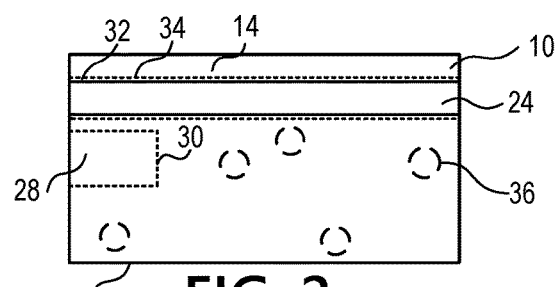
FIG. 2 depicts a rear plan view of the payment card of FIG. 1.

An embodiment of a payment card 10 is illustrated in FIGS. 1-2. Payment card 10 may include a first surface 12 and an opposed second surface 14. A Europay, Mastercard, and Visa (EMV) chip 16 may be positioned on one of first surface 12 and second side 14 of payment card 10. In the illustrated embodiment, EMV chip 22 is positioned on first surface 12 of payment card 10. A magnetic strip 24 may also be positioned on payment card 10. Magnetic strip 24 may be positioned on first surface 12 or on second side 14 of payment card 10, and may be positioned on the same side as EMV chip 22, or on the opposite side. In the illustrated embodiment, magnetic strip 24 is positioned on second side 14. An identification number 26 may be positioned on first surface 12 or on second side 14 of payment card 10. In the illustrated embodiment, identification number 26 is positioned on first surface 12 of payment card 10.

Each of EMV chip 22 and magnetic strip 24 may be removably secured to payment card 10. EMV chip 22 may be positioned in a first portion 28 of payment card 10 that can be removed from payment card 10. In the illustrated embodiment, a first perforation line 30 surrounds first portion 28 allowing first portion 28 of payment card 10 and, therefore, EMV chip 22 to be removed from payment card 10 when payment card is no longer active and is going to be recycled or otherwise discarded.

Magnetic strip 24 may be positioned in a second portion 32 of payment card 10 that can be removed from payment card 10. In the illustrated embodiment, a pair of second perforation lines 34 surrounds second portion 32, allowing second portion 32 of payment card 10 and, therefore, magnetic strip 24 to be removed from payment card 10 when payment card is no longer active and is going to be recycled or otherwise discarded.

One or more plant plant seeds 36 may be embedded within payment card 10. Rather than discarding payment card 10 when it is no longer active, and placing it in the trash, a landfill, or other disposal container, it may be placed in the ground, allowing plant seeds 36 to grow into a plant, and the biodegradable plastic of payment card 10 to decompose. Plant seeds 36 may be pepper plant seeds, pollinator flower plant seeds, or mint plant seeds, for example Other suitable plant seeds 36 to be embedded in payment card 10 will become readily apparent to those skilled in the art, given the benefit of this disclosure. It is to be appreciated that payment card 10 with embedded plant seeds 36 could be planted outdoors in a garden, or in a pot.

Figure 3:
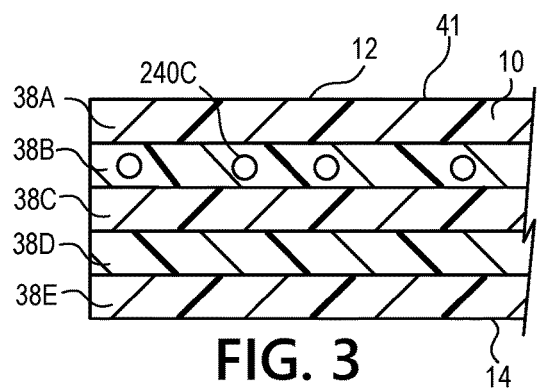
FIG. 3 depicts a partially broken away section view showing layers of the payment card of FIG. 1, and plant seeds in a first layer of the payment card.

In certain embodiments, as illustrated in the partially broken away section view of FIG. 3, payment card 10 may be formed of a plurality of layers 38 of biodegradable plastic. In the illustrated embodiment, payment card 10 may include five layers 38A-E. It is to be appreciated that payment card 10 need not be formed of five layers, and that it may be formed of more or less than five layers.

Figure 4:
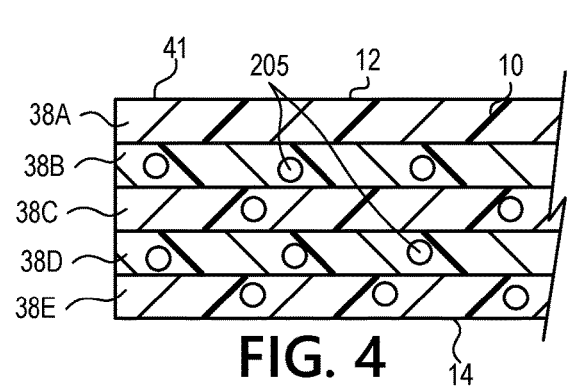
FIG. 4 depicts a partially broken away section view showing layers of an alternative embodiment of the payment card of FIG. 1, and plant seeds in a plurality of layers of the payment card.

In certain embodiments, one or more plant seeds 36 may be located in a first layer 38B of payment card 10. First layer 38B may be adjacent to an outermost layer 38A of payment card 10. In other embodiments, as illustrated in FIG. 4, one or more plant seeds 36 may also be positioned in one or more additional layers of payment card 10. In the illustrated embodiment, plant seeds 36 are positioned in each of layers 38B-E of payment card 10. It is to be appreciated that any number of plant seeds 36 may be positioned in any of layers 38A-E of payment card 10.

Figure 5:
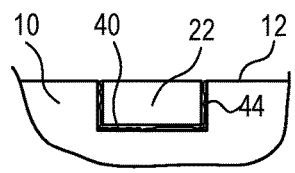
FIG. 5 depicts a section view of a portion an alternative embodiment of the payment card of FIG. 1, showing an EMV chip removably received in a recess in a first surface of the payment card.
Figure 6:
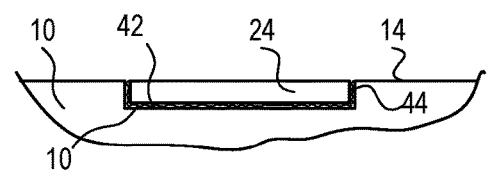
FIG. 6 depicts a section view of the payment card of FIG. 5, showing a magnetic strip received in a recess in a second surface of the payment card.

Another embodiment of payment card is illustrated in FIGS. 5-6, in which EMV chip 22 is seated in a first recess 40 formed in first surface 12 of payment card 10 and extending inwardly from a peripheral edge 41 of payment card 10, and magnetic card 24 is seated in a second recess 42 formed in second surface 14 of payment card 10 and extending inwardly from peripheral edge 41. EMV chip 22 may be removably secured to payment card 10 by being engaged within first recess 40 in snap-fit fashion. In other embodiments, adhesive 44 may be positioned within first recess 40 in order to removably secure EMV chip 22 within first recess 40. Similarly, magnetic strip 24 may be removably secured to payment card 10 by being engaged within second recess 42 in snap-fit fashion. In other embodiments, adhesive 44 may be positioned within second recess 42 in order to removably secure magnetic strip 24 within second recess 42.

Figure 7:
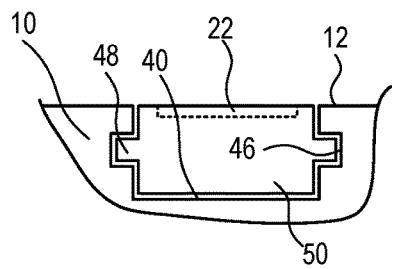
FIG. 7 depicts a section view of a portion an alternative embodiment of the payment card of FIG. 1, showing an EMV chip removably received in a slot in a first surface of the payment card.

Another embodiment of payment card 10 is illustrated in FIG. 7, in which grooves 46 are formed in opposed sides of first recess 40, and mating projections 48 are formed on opposed sides of a first insert 50 that is slidingly received in first recess 40. EMV chip 22 may be positioned in first insert 50, allowing first insert 50 with EMV chip 22 to be removably secured to payment card 10. It is to be appreciated that in other embodiments grooves 48 could alternatively be formed on opposed sides of first insert 50, and that the mating projections 48 could be formed on opposed sides of first recess 40.

Figure 8:
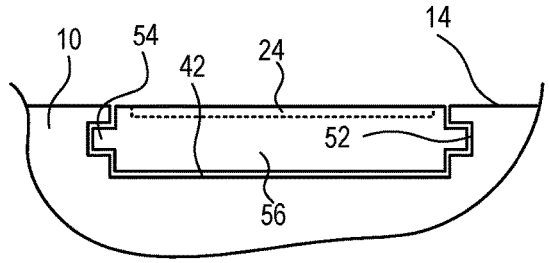
FIG. 8 depicts a section view of the payment card of FIG. 7, showing a magnetic strip removably received in a slot in a second surface of the payment card.

Another embodiment of payment card 10 is illustrated in FIG. 8, in which grooves 52 are formed in opposed sides of second recess 42, and mating projections 54 are formed on opposed sides of a second insert 56 that is slidingly received in second recess 42. Magnetic strip 24 may be positioned in second insert 56, allowing second insert 56 with magnetic strip 24 to be removably secured to payment card 10. It is to be appreciated that in other embodiments grooves 52 could alternatively be formed on opposed sides of second insert 56, and that the mating projections 54 could be formed on opposed sides of second recess 42.

Figure 9:
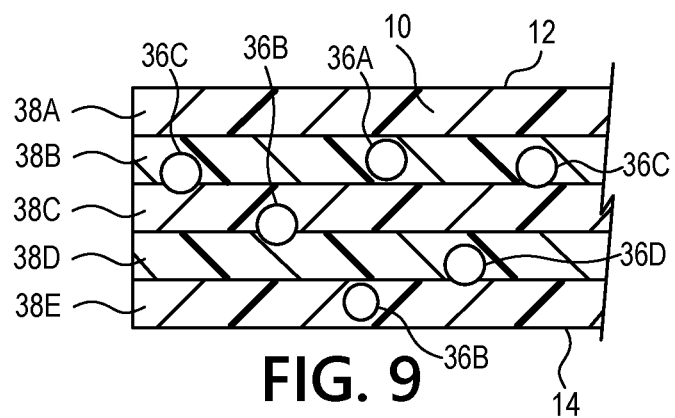
FIG. 9 depicts a partially broken away section view showing layers of an alternative embodiment of the payment card of FIG. 1, and plant seeds in a plurality of layers of the payment card.

Another embodiment of payment card 10 is illustrated in FIG. 9, in which it can be seen that one or more of plant seeds 36 may be positioned completely within a specific layer, while one or more other plant seeds 36 may be positioned in more than one layer. In the illustrated embodiment, a plant seed 36A is positioned completely in layer 38B while another plant seed 36B is positioned completely in layer 38E. Each of a pair of plant seeds 36C is positioned partially in layer 38B and partially in layer 38C. Another plant seed 36D is positioned partially in layer 38D and partially in layer 38E. It is to be appreciated that any number of plant seeds 36 may be positioned completely within a particular layer 38 of payment card 10, and that any number of plant seeds may be positioned in more than one layer 38 of payment card 10.

Thus, while there have been shown, described, and pointed out fundamental novel features of various embodiments, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is the intention, therefore, to be limited only as indicated by the scope of the claims appended hereto.

What is claimed is:

1. A payment card assembly comprising:
a payment card having a first surface, an opposed second surface, and being formed of a biodegradable plastic;
a first recess formed in the first surface of the payment card;
a Europay, Mastercard, and Visa (EMV) chip removably secured to the payment card within the first recess via an adhesive; and
one or more plant seeds embedded in the payment card.

2. The payment card assembly of claim 1, wherein the EMV chip is positioned in a portion of the payment card that is surrounded by a perforation line.

3. The payment card assembly of claim 1, wherein the first recess extends inwardly from a peripheral edge of the payment card, and further comprising an insert removably received in the first recess, grooves extending along opposed sides of one of the first recess and the insert, and mating projections formed on opposed sides of the other of the first recess and the insert, wherein the EMV chip is positioned in the insert.

4. The payment card assembly of claim 1, further comprising a magnetic strip removably secured to the payment card.

5. The payment card assembly of claim 4, further comprising a second recess formed in the first surface of the payment card, the magnetic strip being removably secured within the second recess.

6. The payment card assembly of claim 5, wherein the magnetic strip is removably secured to the payment card within the second recess via an adhesive.

7. The payment card assembly of claim 5, wherein the second recess extends inwardly from a peripheral edge of the payment card, and further comprising an insert removably received in the second recess, grooves extending along opposed sides of one of the second recess and the insert, and mating projections formed on opposed sides of the other of the second recess and the insert, wherein the magnetic strip is positioned in the insert.

8. The payment card assembly of claim 1, wherein the payment card includes a plurality of layers of biodegradable plastic.

9. The payment card assembly of claim 8, wherein the one or more plant seeds is located in a first layer of the plurality of layers of biodegradable plastic, the first layer being adjacent to an outermost layer of the plurality of layers of biodegradable plastic.

10. The payment card assembly of claim 8, wherein a first plant seed is positioned in a first layer of the plurality of layers of biodegradable plastic, and a second plant seed is positioned in a second layer of the plurality of layers of biodegradable plastic.

11. The payment card assembly of claim 8, wherein at least one plant seed is positioned in each layer of the plurality of layers of biodegradable plastic.

12. A payment card assembly comprising:

a payment card having a first surface, an opposed second surface, and being formed of a plurality of layers of biodegradable plastic;

a first recess formed in the first surface of the payment card;

a Europay, Mastercard, and Visa (EMV) chip removably secured to the payment card within the first recess via an adhesive;

a magnetic strip removably secured on the second surface of the payment card; and one or more plant seeds embedded in the payment card.

13. The payment card assembly of claim 12, further comprising a second recess formed in the second surface of the payment card, the magnetic strip being removably secured within the second recess.

14. The payment card assembly of claim 13, wherein the magnetic strip is removably secured to the payment card within the second recess via an adhesive.

15. The payment card assembly of claim 13, wherein:

the first recess extends inwardly from a first peripheral edge of the payment card, the second recess extends inwardly from a second peripheral edge of the payment card, a first insert is removably received in the first recess, a second insert is removably received in the second recess, first grooves extend along opposed sides of one of the first recess and the first insert, first projections are formed on opposed sides of the other of the first recess and the first insert, second grooves extend along opposed sides of one of the second recess and the second insert, second projections are formed opposed sides of the other of second recess and the second insert, the EMV chip is positioned in the first insert, and the magnetic strip is positioned in the second insert.

16. The payment card assembly of claim 12, wherein the one or more plant seeds is located in a first layer of the plurality of layers of biodegradable plastic, the first layer being adjacent to an outermost layer of the plurality of layers of biodegradable plastic.

17. The payment card assembly of claim 12, wherein a first plant seed is positioned in a first layer of the plurality of layers of biodegradable plastic, and a second plant seed is positioned in a second layer of the plurality of layers of biodegradable plastic.

18. A payment card assembly comprising:

a payment card having a first surface, an opposed second surface, a first recess formed in the first surface, a second recess formed in the second surface, and being formed of a plurality of layers of biodegradable plastic;

a Europay, Mastercard, and Visa (EMV) chip removably secured to the payment card within the first recess via an adhesive; and a magnetic strip removably secured in the second recess; and a plurality of plant seeds embedded in a first layer of the plurality of layers of biodegradable plastic, the first layer being adjacent an outermost layer of the plurality of layers of biodegradable plastic.

* * * * *